United States Patent [19]

Kraus et al.

[11] Patent Number: 5,236,473
[45] Date of Patent: Aug. 17, 1993

[54] SIPPER TUBE WITH ULTRASONIC DEBUBBLING

[75] Inventors: Robert P. Kraus, Rochester; Stephen K. Clyde, Clifton Springs; Simon C. Haseler; Edwin J. Voll, both of Rochester, all of N.Y.

[73] Assignee: Eastman Kodak Company, Rochester, N.Y.

[21] Appl. No.: 973,884

[22] Filed: Nov. 10, 1992

[51] Int. Cl.$^5$ .............................................. B01D 51/08
[52] U.S. Cl. ........................................ 95/30; 55/270; 55/277; 73/864.34; 73/864.73; 422/100; 422/128
[58] Field of Search ...................... 55/15, 52, 270, 277; 73/864.34, 864.35, 864.73; 422/100, 128; 436/54

[56] References Cited

U.S. PATENT DOCUMENTS 3,487,697  1/1970  Epstein .
3,737,844  6/1973  Yokoyama et al. .
3,904,392  9/1975  VanIngen et al. .
4,070,167  1/1978  Barbee et al. .
4,205,966  6/1980  Horikawa .
4,612,018  9/1986  Tsuboi et al. .
4,825,688  5/1989  Kraus, Jr. et al. .
5,022,899  6/1991  Hohlfeld et al. .

FOREIGN PATENT DOCUMENTS 2071841A  1/1984  United Kingdom .

Primary Examiner—Charles Hart
Attorney, Agent, or Firm—Carl F. Ruoff

[57] ABSTRACT

The invention is a sampling device (4) and method used to remove bubble free samples from a bubble laden liquid. The device includes a power supply (10), a transducer (6) and a sampling probe (5). The power supply (10) converts normal line voltage to 20 kHz electrical energy. This high frequency electrical energy is converted to mechanical vibrations via the piezoelectric transducer (6). These mechanical vibrations propagate down the sampling probe (5) and emanate from the tip of the probe in the form of ultrasonic waves. The ultrasonic waves emanating from the probe tip serve to push away air bubbles from the vicinity of the tip. This allows the removal of a bubble free sample from the bubble laden liquid for further analysis.

7 Claims, 3 Drawing Sheets

SIPPER TUBE WITH ULTRASONIC DEBUBBLING

FIELD OF THE INVENTION

The present invention relates to a method and apparatus for extracting bubble free samples from a bubble laden liquid for real time testing and analysis.

BACKGROUND OF THE INVENTION

In many instances in the manufacture of photographic emulsions or dispersions, chemical reactions take place over a very short period of time. Most of these reactions take place in kettles or vessels that are undergoing high shear mixing and that contain high levels of entrained air that result from the mixing operation. In order to understand and monitor the chemistry that is taking place, a means is required to extract and deliver for analysis, bubble free samples.

In the past, liquid samples have been manually or automatically extracted and then delivered to the testing lab for analysis. By the time they were analyzed, the bubbles had risen out of the sample by buoyant forces and therefore bubbles in the sample were not a problem. With the advent of online analyzers and the need for immediate information on the state of the reaction, a method is desired to deliver bubble free samples to an analyzer with minimal time delays, ie, approximately 1 to 2 seconds. One such analyzer is described in patent GB 2071841 A.

Various methods have been described in which ultrasonic waves have been used to eliminate bubbles from process fluids. Methods like those described in U.S. Pat. Nos. 3,904,932; 4,612,018 and 5,022,899 require some sort of holdup volume on which the ultrasonic waves act to either redissolve the bubbles or to push the bubbles away. This is not satisfactory for real time analysis of samples as this operation would be too slow for rapid analysis.

A method for redissolving bubbles inline is described in U.S. Pat. No. 4,205,966. As described in this patent, most of the bubbles are eliminated in the holding kettle as they rise to the surface via buoyant forces. The liquid is extracted from the kettle and pressurized. This pressurization along with the application of ultrasonic waves redissolves the bubbles prior to the liquid being used. This method has the drawback that only a small number of bubbles can be eliminated (less than 1000 per minute in 5 liters or 200 bubbles per liter). However, in many systems the reaction liquids may include up to 30% entrained air and the delivery line is not pressurized. Therefore the method described in this patent would not allow the extraction of bubble-free samples in these situations.

A method for creating a bubble free volume in a bubble laden liquid is described in U.S. Pat. No. 4,825,688. This method has the drawbacks that no sample is extracted from the volume, and that the ultrasonic generating crystal is either immersed in the fluid or mounted through the side of the kettle.

The present invention solves the problems of the devices discussed above. Specifically, the present invention allows one to remove a bubble free sample from a bubble laden liquid. In addition the bubble free sample is available for immediate analysis thereby providing real-time information about the characteristics of the bubble laden liquid.

SUMMARY OF THE INVENTION

The present invention is a device for extracting a bubble free sample from a liquid containing bubbles comprising; an ultrasonic transducer; a sampling tube having two ends, mounted at a first end to said transducer and having an inlet port at a second end. Ultrasonic energy from the transducer is transmitted through the sampling tube from the first end to the inlet port, thereby allowing a bubble free volume to be extracted when the device is inserted into a liquid containing bubbles.

In a preferred embodiment, a baffle is formed at the second end of the sampling tube. This baffle helps exclude high energy bubbles from the inlet port.

The present invention is a method of extracting a bubble free sample from a bubble laden liquid comprising positioning within the bubble laden liquid a sampling means having an inlet port, transmitting ultrasonic energy through the sampling means and into the bubble laden liquid such that bubbles within the liquid are pushed away from the inlet port and extracting a bubble free sample from the bubble laden liquid.

In a preferred embodiment of the method described above, the sampling means includes a baffle at the inlet port.

For a better understanding of the present invention, together with other advantages and capabilities thereof, reference is made to the following detailed description and appended claims in connection with the preceding drawings and description of some aspects of the invention.

DETAILED DESCRIPTION OF THE PREFERRED EMBODIMENT

The present invention is a sampling device and method used to remove bubble free samples from a bubble laden liquid. The device includes a power supply, a transducer and a sampling probe. The power supply converts 50/60 Hz line voltage to 20 kHz electrical energy. This high frequency electrical energy is converted to mechanical vibrations via a piezoelectric transducer. These mechanical vibrations are transmitted down the sampling probe and emanate from the tip of the probe in the form of ultrasonic waves. The amplitude of these waves can be adjusted by control of the power supply.

By this technique, the ultrasonic waves emanating from the probe tip serve to push away bubbles from the vicinity of the tip. In a preferred embodiment of the invention, the probe tip includes an integral baffle, the purpose of the baffle being the partial exclusion of additional air bubbles from the vicinity of the tip. While this exclusion is occurring, the flow of the liquid in the kettle along with any particles dispersed in the liquid is unimpaired in its access to the probe tip. This advantageous since it allows for representative sampling of the kettle contents for various analytical measurements.

In an alternate embodiment which can be used with or without the integral baffle, the probe tip having a channel machined in its center is connected to a side arm hose barb fitting. The purpose of said channel is to allow the bubble free liquid to be drawn from the probe tip area to the hose barb from whence a fluid transport system can deliver the liquid to an online analytical instrument. Another feature of this invention is the very small dead volume within the channel and the hose barb, this being approximately 2 milliliters. This small dead volume combined with a flow rate of a 100 milliliters per minute allows for quick transfer of the sample from the kettle to the analytical instrument, thereby allowing for real time analytical measurements. Further, the machining of the exterior of the probe and its channel is done in such a way as to focus the ultrasonic waves at the probe tip thus allowing for the most effective means of pushing the bubbles away from the tip.

Figure 1:
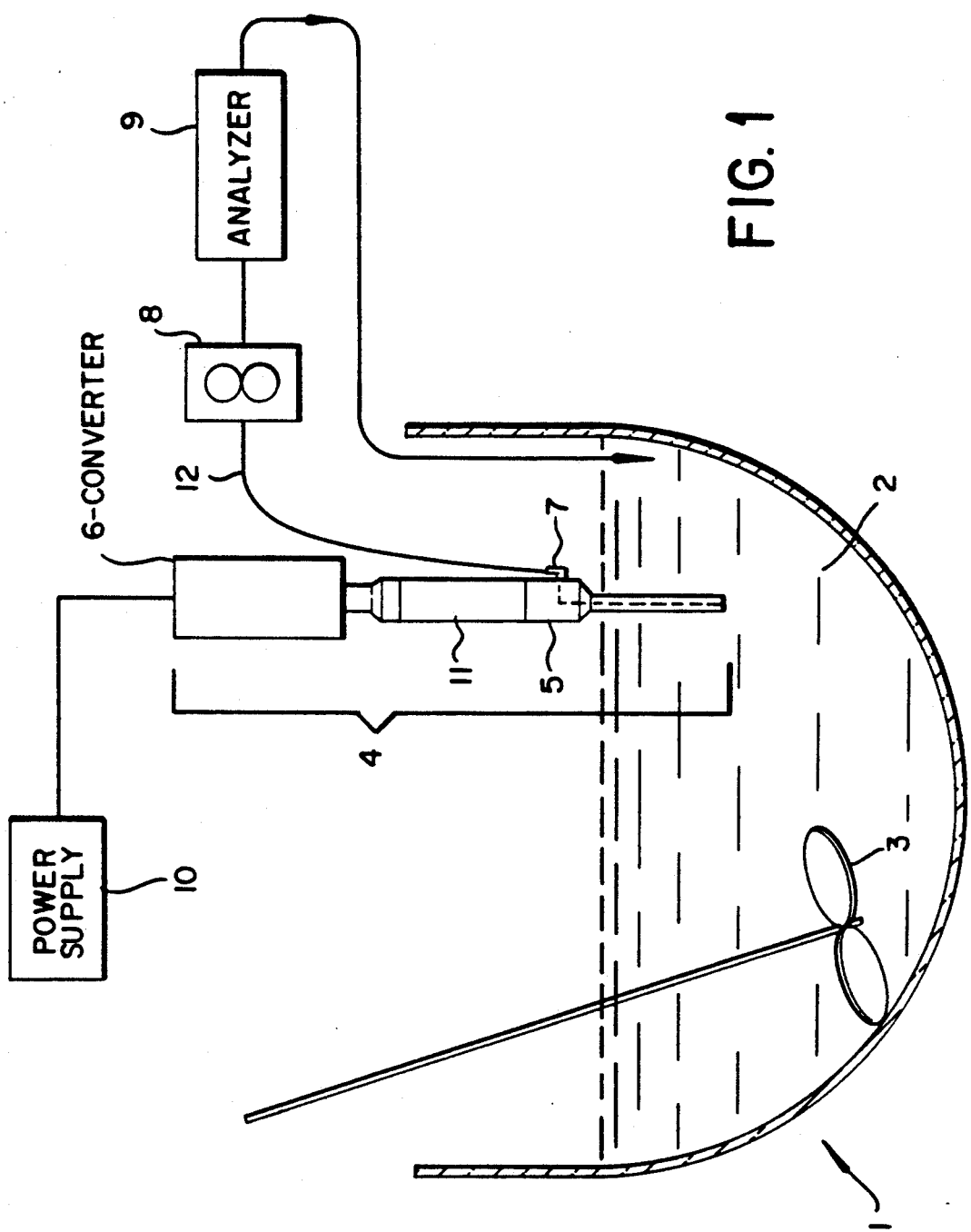
FIG. 1 shows the bubble eliminator sampling tube of the present invention immersed in a reaction kettle.

The present invention will now be described with reference to the accompanying drawings. FIG. 1 shows the bubble eliminating sampling tube (BEST) located in a kettle in its normal configuration for withdrawing bubble free samples for delivery to an analyzer. Referring to FIG. 1, a kettle 1 with an agitator 3 is shown. The agitator 3 can be rotated at such a speed as to create a substantial amount of entrained air in the form of air bubbles in the process within the kettle 1. The BEST 4 is positioned in the kettle so that the probe tip 5 is below the surface of the reaction liquid 2 and the ultrasonic transducer assembly including the convertor 6, is above the surface. In operation, the BEST 4 can be positioned anywhere in the kettle as long as the above criteria are met and the tip is not located in a vortex, in which case there is no fluid to debubble. In operation, the BEST is preferably mounted in a vertical position. The BEST should only be held or attached to external support brackets at the convertor 6. Attachment or connections to any other part of the BEST, except at the hose barb 7 will reduce the efficiency of the device. A rigid tube or flexible hose 12 is connected to hose barb 7. A pump 8 is connected to the hose 12 which in turn is connected to an analyzer 9. The analyzer can be any number of commercial or custom built real time analyzers for performing physical or chemical measurements on the debubbled liquid (eg, particle size, chemical composition, etc.). From the analyzer, the liquid is either returned to the reaction kettle or sent to waste.

When the ultrasonic power supply 10 is turned on, the convertor 6 generates ultrasonic waves which are transmitted through the extension rod 11 and probe tip 5 into liquid surrounding the probe tip 5. The probe tip 5 is actually a tubular structure which provides a flow path from the probe tip to the hose barb 7 attached to the lower side of the tip assembly. With tubing attached to the hose barb a flow path with minimum holdup volume is provided between the bubble free volume at the end of the tip through the pump to the analyzer.

A power supply 10 drives a convertor 6 which converts electrical energy to ultrasonic energy. The energy is carried through the extender rod 11 to the probe tip 5 and ultimately into the fluid surrounding the probe tip. The construction of the power supply convertor and extender rod 11 are well known in the ultrasonic processing industry and can be purchased from any number of vendors. The particular unit of the present invention included a Vibra-Cell Model VC50AT and was purchased from Sonics and Material Inc. Commercial equipment normally operates in the frequency range of 20 kHz to 40 kHz with the geometry of the various ultrasonic components being directly related to the operating frequency as is well known in the field. The extender rod 11 and probe tip 5 can be constructed of any suitable material such as stainless steel or titanium. Titanium, however is the preferred material because of its good ultrasonic properties and its resistance to corrosion.

Figure 2:
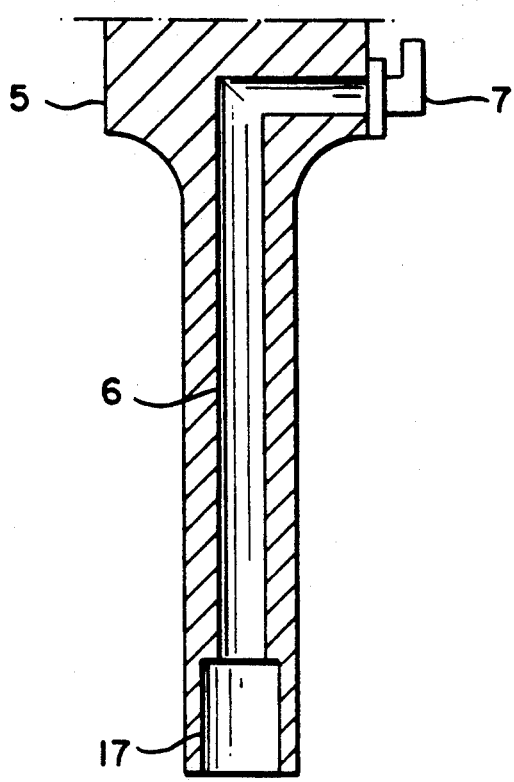
FIG. 2 shows a detailed view of the bubble eliminator sampling tube and baffle of the present invention.
Figure 3:
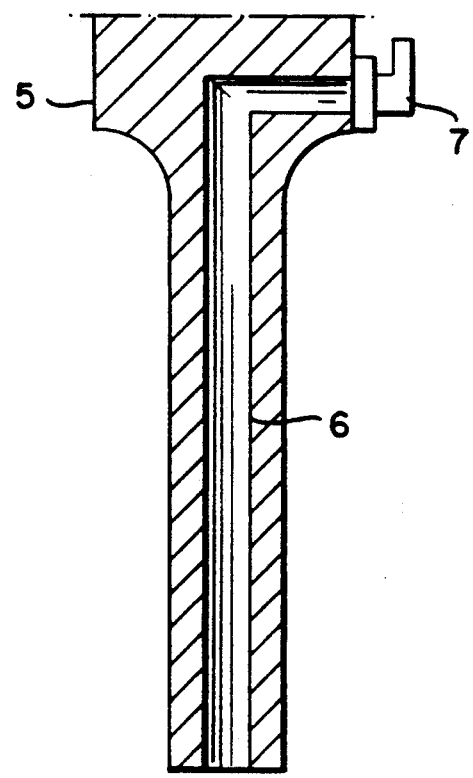
FIG. 3 shows a detailed view of the bubble eliminator sampling tube without baffle of the present invention.

One of the novel features of the present invention is the probe tip 5 shown in cross section in FIGS. 2 and 3. For the present application the tip was designed to operate at 20 kHz. However, the tip can be modified to operate at any frequency by those skilled in the construction of ultrasonic probe tips or horns. The key features of this probe tip are: 1) the location of the hose barb at an ultrasonic nodal point of the tip, at a point of minimum ultrasonic activity; 2) a hole bored through the center of the tip connecting the hose barb and the end of the tip; and preferably 3) a large opening or baffle arrangement 17 (FIG. 2) machined into the probe tip or horn. These three features can be incorporated into the design of a tip so as to maximize the transfer of ultrasonic energy into the surrounding liquid while at the same time minimizing any adverse ultrasonic effects (erosion, cracking, heating, corrosion, etc.) along the length of the probe tip and in the area of the hose barb by anyone skilled in the manufacture of ultrasonic tools and tips. FIGS. 2 and 3 both show probe tips 5 or horns having an internal channel 6 connected to a hose barb 7. FIG. 2 shows a probe tip 5 which includes a baffle 17 at the end of the probe tip.

In practice, the ultrasonic energy that propagates down through the extender rod 11 and the probe tip 5 and radiates into the liquid, pushes bubbles away from the small volume in the vicinity of the probe tip. In a kettle that is not being aggressively mixed and has low bubble velocities, a normal unbaffled horn tip (FIG. 3) is sufficient. The radiated ultrasonic energy pushes the bubbles away from the horn tip and keeps them away since the bubbles do not have enough energy to penetrate the ultrasonic field. However, with higher mixing rates and the associated high velocity bubbles, a baffle is required in order to keep stray bubbles from reentering the bubble free zone which is created within the baffle volume.

Since liquid is being extracted from the bubble free volume for analysis downstream in the analyzer, there is also the possibility the bubbles can be drawn back into the bubble free volume with the liquid that is replacing the bubble free liquid that is being withdrawn. The baffle helps prevent this possibility. The overall ability to provide bubble free liquid to the analyzer is dependent on the fluid extraction rate and can be increased by increasing the applied ultrasonic energy, the size of the probe tip or horn, or operating in lower entrained air level reactions.

Figure 4:
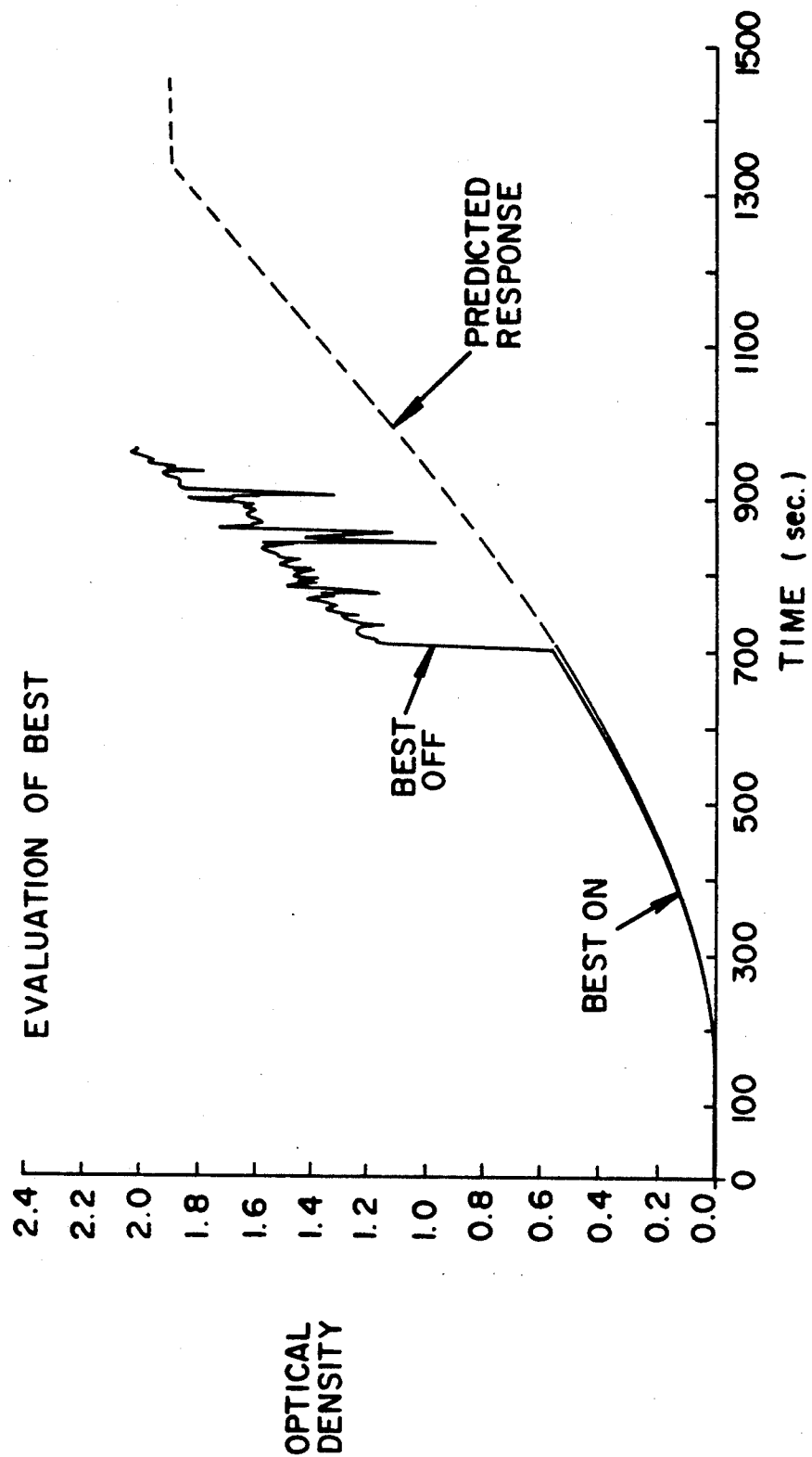
FIG. 4 shows a plot of optical density versus time using bubble eliminator sampling tube of the present invention.

FIG. 4 shows the impact of the BEST on the output of an analyzer during an actual chemical reaction in a kettle being mixed at a high shear rate. The test setup is as shown in FIG. 1. In this particular example the analyzer measured optical density to determine the state of the reaction. The reaction was conducted in a kettle containing 18 liters of reactant mixture. The mixing rate was approximately 6000 rpm. The extraction rate was approximately 100 ml/min. through the BEST. The entire reaction is relatively short, running to completion in less than 1500 seconds. The reaction was initiated with the BEST turned on and an increase in optical density with reaction time was observed. At about 700 seconds into the reaction, the BEST was turned off. Bubble laden liquid began flowing into the analyzer and the analyzer reported erroneously high and noisy results. The dotted line indicates the expected response of the analyzer to the reaction as it progresses towards completion.

While there has been shown and described what are at present considered the preferred embodiments of the invention, it will be obvious to those skilled in the art that various changes, alterations and modifications may be made therein without departing from the scope of the invention as defined by the appended claims.

What is claimed:

1. A device for extracting a bubble free sample from a liquid containing bubbles comprising:
   an ultrasonic transducer;
   a sampling tube having two ends mounted at a first end to said transducer and having an inlet port at a second end;
   wherein ultrasonic energy from said transducer is transmitted through said sampling tube from the first end to the inlet port whereby when said sampling tube is immersed said liquid containing bubbles, bubbles are forced away from the inlet port; and
   extraction means for removing a liquid sample through said sampling tube.

2. The device according to claim 1 wherein said ultrasonic transducer is capable of transmitting energy at a frequency of about 25 kHz to about 40 kHz.

3. A device for extracting a bubble free sample from a liquid containing bubbles comprising:
   an ultrasonic transducer;
   a sampling tube having two ends mounted at a first end to said transducer and having an inlet port at a second end wherein a baffle is formed at the second end of said sampling tube;
   wherein ultrasonic energy from said transducer is transmitted through said sampling tube from the first end to the inlet port whereby when said sampling tube is immersed in said liquid containing bubbles, bubbles are forced away from the inlet port; and
   extraction means for removing a liquid sample through said sampling tube.

4. The device according to claim 3 wherein said ultrasonic transducer is capable of transmitting energy at a frequency of about 25 kHz to about 40 kHz.

5. A method of extracting a bubble-free sample from a bubble laden liquid, comprising:
   positioning within the bubble laden liquid a sampling means having an inlet port;
   transmitting ultrasonic energy through said sampling means and into the bubble-laden liquid such that bubbles within the liquid are pushed away from the inlet port;
   extracting a bubble-free sample from the liquid near the inlet port.

6. The method according to claim 5 further comprising analyzing the particle size of the extracted bubble-free sample.

7. The method according to claim 5 further comprising baffling said liquid at said inlet port.

* * * * *